(12) United States Patent
Atkinson et al.

(10) Patent No.: US 8,758,761 B2
(45) Date of Patent: Jun. 24, 2014

(54) COMBINATION THERAPIES FOR TREATING TYPE 1 DIABETES

(75) Inventors: Mark A. Atkinson, Gainesville, FL (US); Scott Eisenbeis, Cambridge, MA (US); Donna Armentano, Cambridge, MA (US); Abraham Scaria, Cambridge, MA (US); Tracey Lodie, Cambridge, MA (US)

(73) Assignees: University of Florida Research Foundation, Inc., Gainesville, FL (US); Genzyme Corporation, Cambridge, MA (US)

( * ) Notice: Subject to any disclaimer, the term of this patent is extended or adjusted under 35 U.S.C. 154(b) by 442 days.

(21) Appl. No.: 12/680,614

(22) PCT Filed: Sep. 30, 2008

(86) PCT No.: PCT/US2008/078286
§ 371 (c)(1),
(2), (4) Date: Sep. 10, 2010

(87) PCT Pub. No.: WO2009/046015
PCT Pub. Date: Apr. 9, 2009

(65) Prior Publication Data
US 2010/0322894 A1  Dec. 23, 2010

Related U.S. Application Data

(60) Provisional application No. 60/976,442, filed on Sep. 30, 2007.

(51) Int. Cl.
*A61K 39/00* (2006.01)
*A61K 39/38* (2006.01)

(52) U.S. Cl.
USPC ................................... 424/184.1; 424/185.1

(58) Field of Classification Search
None
See application file for complete search history.

(56) References Cited

U.S. PATENT DOCUMENTS

| | | | |
|---|---|---|---|
| 4,810,643 A | 3/1989 | Souza | |
| 4,904,584 A | 2/1990 | Shaw | |
| 5,104,651 A | 4/1992 | Boone et al. | |
| 5,116,753 A * | 5/1992 | Beattie et al. | 435/34 |
| 5,214,132 A | 5/1993 | Kuga et al. | |
| 5,218,092 A | 6/1993 | Sasaki et al. | |
| 5,362,853 A | 11/1994 | Kuga et al. | |
| 5,574,008 A | 11/1996 | Johnson et al. | |
| 5,606,024 A | 2/1997 | Boone et al. | |
| 5,624,895 A * | 4/1997 | Sobel | 424/85.4 |
| 5,824,778 A | 10/1998 | Ishikawa et al. | |
| 5,824,784 A | 10/1998 | Kinstler et al. | |
| 6,017,876 A | 1/2000 | Gegg et al. | |
| 6,166,183 A | 12/2000 | Ishikawa et al. | |
| 6,261,550 B1 | 7/2001 | Osslund | |
| 6,534,272 B2 * | 3/2003 | Polychronakos et al. | 435/6.11 |
| 7,220,407 B2 | 5/2007 | Mehta et al. | |
| 2003/0064922 A1 | 4/2003 | Nissen et al. | |
| 2004/0209801 A1 * | 10/2004 | Brand et al. | 514/12 |
| 2006/0153894 A1 | 7/2006 | Ghabrial et al. | |
| 2006/0189520 A1 | 8/2006 | Brand et al. | |

FOREIGN PATENT DOCUMENTS

| | | |
|---|---|---|
| AU | 76380/91 | 11/1991 |
| AU | 10948/92 | 8/1992 |
| EP | 0243153 | 10/1987 |
| EP | 0256843 | 2/1988 |
| EP | 0272703 | 6/1988 |
| EP | 0335423 | 10/1989 |
| EP | 0401384 | 12/1990 |
| EP | 0459630 | 12/1991 |
| WO | WO 9012874 | 11/1990 |
| WO | WO 2007041368 | 4/2007 |
| WO | WO 2007064757 | 6/2007 |

OTHER PUBLICATIONS

Bacigalupo, A, "Antithymocyte globulin for prevention of graft-versus-host diasese," *Curr Opin Hematol.*, 2005, pp. 457-462, vol. 12.
Bevans, et al. "Management of patients receiving antithymocyte globulin for aplastic anemia and myelodysplastic syndrome," *Clin J Oncol Nurs.*, 2004, pp. 377-382, vol. 8.
Kuga, et al., "Mutagenesis of human granulocyte colony stimulating factor," *Biochem. Biophys. Res. Comm.*, 1989, pp. 103-111, vol. 159.
Lu, et al., "Disulfide and secondary structures of recombinant human granulocyte colony stimulating factor," *Arch. Biochem. Biophys.* 1989, pp. 81-92, vol. 268.
Nashan, B., "Antibody induction therapy in renal transplant patients receiving calcineurin-inhibitor immunosuppressive regimens: a comparative review," *BioDrugs*, 2005, pp. 39-46, vol. 19.
Smith, et al., "Current immunosuppressive agents: efficacy, side effects, and utilization," *Pediatr Clin North Am*, 2003, pp. 1283-1300, vol. 50.

\* cited by examiner

*Primary Examiner* — Michail Belyavskyi
(74) *Attorney, Agent, or Firm* — Saliwanchik, Lloyd & Eisenschenk

(57) ABSTRACT

In accordance with the subject invention, combination therapies can be used to modulate a patient's immune response in order to prevent, delay and/or reverse type 1 diabetes.

16 Claims, No Drawings

COMBINATION THERAPIES FOR TREATING TYPE 1 DIABETES

CROSS-REFERENCE TO A RELATED APPLICATION

This application is a National Stage Application of International Application Number PCT/US2008/078286, filed Sep. 30, 2008; which claims the benefit of U.S. Provisional Application No. 60/976,442, filed Sep. 30, 2007, which are incorporated herein by reference in their entirety.

BACKGROUND OF THE INVENTION

Diabetes mellitus is a family of disorders characterized by chronic hyperglycemia and the development of long-term vascular complications. This family of disorders includes type 1 diabetes, type 2 diabetes, gestational diabetes, and other types of diabetes.

Immune-mediated (type 1) diabetes (or insulin dependant diabetes mellitus, IDDM) is a disease of children and adults for which there currently is no adequate means for treatment or prevention. Type 1 diabetes, represents approximately 10% of all human diabetes. The disease is characterized by an initial leukocyte infiltration into the pancreas that eventually leads to inflammatory lesions within islets, a process called "insulitis".

Type 1 diabetes is distinct from non-insulin dependent diabetes (NIDDM) in that only the type 1 form involves specific destruction of the insulin producing beta cells of the islets of Langerhans. The destruction of beta cells appears to be a result of specific autoimmune attack, in which the patient's own immune system recognizes and destroys the beta cells, but not the surrounding alpha cells (glucagon producing) or delta cells (somatostatin producing) that comprise the pancreatic islet. The progressive loss of pancreatic beta cells results in insufficient insulin production and, thus, impaired glucose metabolism with attendant complications.

The factors responsible for type 1 diabetes are complex and thought to involve a combination of genetic, environmental, and immunologic influences that contribute to the inability to provide adequate insulin secretion to regulate glycemia.

The natural history of type 1 diabetes prior to clinical presentation has been extensively studied in search of clues to the etiology and pathogenesis of beta cell destruction. The prediabetic period may span only a few months (e.g., in very young children) to years (e.g., older children and adults). The earliest evidence of beta cell autoimmunity is the appearance of various islet autoantibodies. Metabolically, the first signs of abnormality can be observed through intravenous glucose tolerance testing (IVGTT). Later in the natural history of the disease, the oral glucose tolerance test (OGTT) typically becomes abnormal. With continued beta cell destruction and frank insulinopenia, type 1 diabetes becomes manifest.

Type 1 diabetes occurs predominantly in genetically predisposed persons. Concordance for type 1 diabetes in identical twins is 30-50% with an even higher rate of concordance for beta cell autoimmunity, as evidenced by the presence of islet autoantibodies in these individuals (Pyke, D. A., 1979. "Diabetes: the genetic connections." *Diabetologia* 17: 333-343). While these data support a major genetic component in the etiopathogenesis of type 1 diabetes, environmental or non-germline genetic factors must also play important pathologic roles. Environmental factors proposed to date include viral infections, diet (e.g., nitrosamines in smoked meat, infant cereal exposure), childhood vaccines, breast-feeding, and early exposure to cows' milk. Hence, while the list of potential environmental agents for type 1 diabetes is large, the specific environmental trigger(s) that precipitate beta cell autoimmunity remain elusive.

Type 1 diabetes is currently managed by the administration of exogenous human recombinant insulin. Although insulin administration is effective in achieving some level of euglycemia in most patients, it does not prevent the long-term complications of the disease including ketosis and damage to small blood vessels, which may affect eyesight, kidney function, blood pressure and can cause circulatory system complications.

Although knowledge of the immune system has become much more extensive in recent years, the precise etiology of type 1 diabetes remains a mystery. Furthermore, despite the enormously deleterious health and economic consequences, and the extensive research effort, there currently is no effective means for controlling the formation of this disease.

BRIEF SUMMARY

The subject invention pertains to the use of combination therapies to prevent, delay and/or reverse type 1 diabetes.

In a preferred embodiment, the combination therapy of the subject invention includes three components—a component that reduces the pathological autoimmune response, a component that promotes beta cell regeneration, and a component that protects beta cell mass.

Immunomodulators useful according to the subject invention include, but are not limited to, anti-thymocyte globulin (ATG), stem cells (preferably mesenchymal stem cells), and rapamycin.

In an embodiment specifically exemplified herein, ATG is used as an immunomodulator in conjunction with other agents. In a particularly preferred embodiment, ATG is used in conjunction with mesenchymol stem cells and granulocyte colony stimulating factor (G-CSF).

The agent used to promote beta cell regeneration may be, for example, G-CSF, exenatide (Byetta®), DPPIV inhibitors (Januvia, etc), EGF+Gastrin, INGAP and/or a local cytokine. The agent used to promote beta cell regeneration may function, for example, by stimulating the bone marrow to produce granulocytes and stem cells via G-CSF.

Agents that can be used to protect beta cell mass include, for example, alpha-1 antitrypsin (AAT), vitamin D, anti-oxidants, anti-inflammatory agents, and modulators of cytokines.

In certain embodiments a single agent may perform multiple functions in the combination therapy of the subject invention. Thus, one preferred embodiment comprises the administration of mesenchymal stem cells (MSCs). The MSCs can contribute to beta cell regeneration, protect beta cell mass, and/or provide advantageous modulation of the autoimmune response.

In one embodiment of the subject invention, the therapies can be administered to a patient prior to the clinical manifestation of type 1 diabetes thereby preventing or delaying the onset of overt disease. In this regard, sufficient beta cell mass exists in certain cases near the time of symptomatic onset such that intervention as described herein enables the patient to retain pancreatic insulin production thereby eliminating or reducing the need for insulin injections. The therapies of the subject invention can also be used to reverse type 1 diabetes.

DETAILED DISCLOSURE

The subject invention pertains to the use of combination therapies to prevent, delay and/or reverse type 1 diabetes.

In a preferred embodiment, the combination therapy of the subject invention includes three components—a component that reduces the pathological autoimmune response, a component that promotes beta cell regeneration, and a component that protects beta cell mass.

Immunomodulators useful according to the subject invention include, but are not limited to, anti-thymocyte globulin (ATG), stem cells, and rapamycin. The stem cells may be administered as cord blood or, preferably as mesenchymol stem cells (MSC).

The agent used to promote beta cell regeneration may be, for example, granulocyte colony-stimulating factor (G-CSF), exenatide (Byetta®), DPPIV inhibitors (Januvia, etc), EGF+Gastrin, INGAP and/or a local cytokine. The agent used to promote beta cell regeneration may function, for example, by stimulating the bone marrow to produce granulocytes and stem cells via G-CSF.

Agents that can be used to protect beta cell mass include, for example, alpha-1 antitrypsin (AAT), vitamin D, anti-oxidants, anti-inflammatory agents, and modulators of cytokines.

Advantageously, in accordance with the subject invention, therapy can be administered to a patient prior to the clinical manifestation of type 1 diabetes thereby preventing or delaying the onset of overt disease. In this regard, sufficient beta cell mass exists in certain cases near the time of symptomatic onset such that intervention, as described herein, enables the patient to retain pancreatic insulin production thereby eliminating or reducing the need for insulin injections. The therapies of the subject invention can also be used to reverse type 1 diabetes, preferably in new-onset patients.

In an embodiment specifically exemplified herein ATG is used as an immunomodulator. Thus, in accordance with one embodiment of the subject invention ATG can be used in combination with other agents to modulate a patient's immune response in order to prevent, delay, and/or reverse type 1 diabetes. Specifically exemplified herein is the use of ATG with mesenchymal stem cells (MSCs) and G-CSF.

Anti-Thymocyte Globulin

ATG is an infusion of rabbit-derived antibodies against human T cells that has been used in the past for the prevention and treatment of acute rejection in organ transplantation and therapy of aplastic anemia. ATG is available, for example, from Genzyme under the trademark of Thymoglobulin®.

ATG has long been known to deplete lymphocytes in vivo and can effectively be used in a variety of therapeutic settings including renal transplantation, graft versus host disease, and aplastic anemia. (Smith, J. M., Nemeth, T. L., and McDonald, R. A. 2003. Current immunosuppressive agents: efficacy, side effects, and utilization. *Pediatr Clin North Am* 50:1283-1300; Nashan, B. 2005. Antibody induction therapy in renal transplant patients receiving calcineurin-inhibitor immunosuppressive regimens: a comparative review. *BioDrugs* 19:39-46; Bevans, M. F., and Shalabi, R. A. 2004. Management of patients receiving antithymocyte globulin for aplastic anemia and myelodysplastic syndrome. *Clin J Oncol Nurs* 8:377-382; Bacigalupo, A. 2005. Antithymocyte globulin for prevention of graft-versus-host disease. *Curr Opin Hematol* 12:457-462). ATG affects a wide range of immune system cells and contains antibodies against many cell surface molecules.

The use of ATG in the treatment of type 1 diabetes and other autoimmune conditions has been disclosed in International Patent Publication No. WO 2007/064757 A1, which is incorporated herein, in its entirety, by reference.

In preferred embodiments of the subject invention, administration of ATG is accompanied by administration of one or more compounds that promote repair, production, preservation and/or regeneration of beta cells. The agent that promotes the repair, production, preservation and/or regeneration of beta cells may be, for example stem cells, cytokines (such as G-CSF), glulisinc, glucagons such as glucagon-like peptide-1 (GLP-1), DPP4 inhibitors, islet regeneration molecules, anti-apoptotic molecules and exendin-4.

Granulocyte Colony-Stimulating Factor

Granulocyte Colony-Stimulating Factor (G-CSF or GCSF) is a hormone produced by a number of different tissues to stimulate the bone marrow to produce granulocytes and stem cells. G-CSF then stimulates the bone marrow to pulse them out of the marrow into the blood. It also stimulates the survival, proliferation, differentiation, and function of neutrophil precursors and mature neutrophils.

G-CSF is produced by endothelium, macrophages, and a number of other immune cells. The natural human glycoprotein exists in two forms, a 174- and 180-amino-acid-long protein of molecular weight 19,600 grams per mole. The more-abundant and more-active 174-amino acid form has been used in the development of pharmaceutical products by recombinant DNA (rDNA) technology.

G-CSF can be isolated from natural sources, produced recombinantly, and obtained from commercial sources under, for example, the tradenames Neupogen®, Granocyte®, and Neulasta®.

The term "G-CSF" as used herein is defined as naturally occurring human and heterologous species G-CSF, recombinantly produced G-CSF that is the expression product consisting of either 174 or 177 amino acids, or fragments, analogs, variants, or derivatives thereof as reported, for example in Kuga et al., Biochem. Biophys. Res. Comm. 159: 103 111 (1989); Lu et al., Arch. Biochem. Biophys. 268: 81 92 (1989); U.S. Pat. Nos. 4,810,643, 4,904,584, 5,104,651, 5,214,132, 5,218,092, 5,362,853, 5,606,024, 5,824,778, 5,824,784, 6,017,876, 6,166,183, and 6,261,550;U.S. patent application No. U.S. 2003/0064922; EP 0 335423; EP 0 272703; EP 0 459630; EP 0 256843; EP 0 243153; WO 9102874; Australian Application document Nos. AU-A-10948/92 and AU-A-76380/91. Included are chemically modified G-CSFs, see, e.g., those reported in WO 9012874, EP 0 401384 and EP 0 335423. See also, WO 03006501; WO 03030821; WO 0151510; WO 9611953; WO 9521629; WO 9420069; WO 9315211; WO 9305169; JP 04164098; WO 9206116; WO 9204455; EP 0 473268; EP 0 456200; WO 9111520; WO 9105798; WO 9006952; WO 8910932; WO 8905824; WO 9118911; and EP 0 370205. Also encompassed herein are all forms of G-CSF, such as ALBUGRANIN®, NEU-ULASTA®, NEUPOGEN®, and GRANOCYTE®.

Formulations and methods for administering G-CSF are well known in the art and are described at, for example, U.S. Pat. No. 7,220,407, which is incorporated herein, in its entirety, by reference.

Mesenchymal Stem Cells

Adult stem cells are undifferentiated cells found amongst differentiated cells in a tissue or organ. They are self-renewable and can differentiate to yield specialized cell types of the specific tissue or organ in which they are found; their primary role is to maintain and repair tissue. Unlike embryonic stem cells, which are defined by their origin, the origin o f adult stem cells in mature tissues is unknown.

MSCs are multipotent progenitor cells that have the potential to give rise to cells of various lineages, including bone, cartilage, and adipose tissues. The type of MSCs that has been the subject of most studies is the bone marrow-derived MSC, although in recent years other tissue sources of these cells have also been analyzed. Since the first description of their isolation by Friedenstein et al, their method for isolation has become standard for the isolation of MSCs. This MSC isolation method is based on the adherence of fibroblast-like cells (recovered from bone marrow) to the plastic substrate of the cell culture plate, along with a parallel lack of adherence of marrow-derived hematopoietic cells. MSCs therefore have the singular ability within the BM population to adhere to tissue culture dishes and can also fully differentiate into several cell lines. MSCs have been characterized in humans and in several animal models.

A battery of negative and positive markers is generally used to characterize these cells, as MSCs lack specific cell surface markers for hematopoietic cells (CD14, CD34, CD11a/LFA-1, CD45), red blood cells (glycophorin A), and endothelial cells (CD31), but express SH2 (CD105), SH3, SH4 (CD73), SB-10, and a group of other adhesion molecules and growth factor/cytokine receptors including CD166, CD54, CD102, CD121a and -b, CD123, CD124, CD49. Although in bone marrow MSCs represent a rare population of cells that make up only 0.001% to 0.01% of total nucleated cells and are 10-fold less abundant than hematopoietic stem cells (HSCs), they nevertheless can be readily grown and expanded in culture.

MSCs can act in vivo through a tri-cell interaction (with DC and Tregs) thereby modulating the immune system. Adding specific relevant immunosuppressants that silence autoreactive T cells can be used according to the subject invention to increase the ability of MSCs to abrogate the autoimmune response.

Advantageously, when MSCs are used in conjunction with other agents in accordance with the subject invention it is possible to utilize lower dosages of the other agents thereby reducing undesirable side effects. Agents that can be used with MSCs include, in addition to ATG and G-CSF, rapamycin, CTLA4-Ig and anti-cD3.

Rapamycin has been extensively used in both pre-clinical and clinical studies, for its well-known immunosuppressive ability and low adverse effect profile. Furthermore, Rapamycin boosts Tregs generation. CTLA4-Ig has been shown to delay both acute and chronic rejection. Anti-CD3 has been shown to be capable of restoring normoglycemia in NOD mice. The major problem with CD3 specific antibodies is the persistence of many adverse effects observed in patients. In accordance with the subject invention lower doses can be used in conjunction with the use of MSCs.

MSCs can be isolated using techniques known in the art and/or they can be obtained commercially from, for example, Osiris Therapeutics, Inc.

Other Agents

In one embodiment of the subject invention, the compound that promotes regeneration and/or repair of beta cells is glulisine. Glulisine is a recombinant insulin analog that has been shown to be equipotent to human insulin. One unit of glulisine has the same glucose-lowering effect as one unit of regular human insulin. Glulisine, as is known in the art, can be administered by subcutaneous injection. After subcutaneous administration, it has a more rapid onset and shorter duration of action.

Another compound that can be administered to promote beta cell regeneration, repair and/or functionality is glucagon-like peptide-1 (GLP-1). Glucagon-like peptide and GLP derivatives are intestinal hormones that generally simulate insulin secretion during hyperglycemia, suppresses glucagons secretion, stimulate (pro) insulin biosynthesis and decelerate gastric emptying and acid secretion. Some GLPs and GLP derivatives promote glucose uptake by cells but do not stimulate insulin expression as disclosed in U.S. Pat. No. 5,574,008 which is hereby incorporated by reference.

The GLP-1 used according to the subject invention may be GLP-1 (7-36), GLP-1 (7-37) or GLP-1 (1-37), or variants thereof. GLP-1 is rapidly metabolized by a peptidase (dipeptidylpeptidase IV or DPP-IV). One way to counter the rapid degradation of the hoiiiione is to couple it to a fatty acid. Liraglutide is such a preparation. Liraglutide binds to serum albumin and is a poor substrate for the peptidase. Single injections of liraglutide give therapeutically active blood levels for 8 to 15 hours.

In a further embodiment, ATG can be administered with a GLP-1 agonist and/or GLP-1 receptor agonist. This agonist compound may be, for example, GPL-1 or exendin-4. Another GLP-1R agonist is Liraglutide. Other gut hormones that promote proliferation of islet beta cells can also be used as can compounds that activate epideiinal growth factor receptor (EGFR) and the cyclic AMP-dependent transcription factor CREB.

Exendin-4 has a longer half-life than GLP-1 and has recently been shown to have a hypoglycemic effect in humans when given twice a day for one month. Exenatide is a 39-amino acid peptide which closely resembles exendin-4. It is DPP-4 resistant and has many of the actions of GLP-1. That is, it slows stomach emptying, increases satiety and decreases food intake and leads to increased release and synthesis of insulin.

As noted above, another agent that can be used according to the subject invention is Alpha 1-Antitrypsin or $\alpha_1$-antitrypsin (AAT), which is a glycoprotein and generally known as serum trypsin inhibitor. AAT is a single chain glycoprotein consisting of 394 amino acids in the mature form. Produced by hepatocytes, AAT functions to inhibit several proteases. It also has anti-inflammatory effects, and protects against tissue damage or injury. The FDA has approved the use of three AAT products derived from human plasma: Prolastin, Zemaira and Aralast. Other compounds that can be delivered according to the subject invention include those that prevent or reduce β cell apoptosis. Vitamin D and prolastin are but two of these examples.

Hormones, such as prolactin, as well as anti-inflammatory agents can also be used as part of the combination therapy of the subject application.

It should also be noted that, in one embodiment, cord blood can be used as a source for stem cells.

Further, the therapy of the subject invention can include antigen therapy. The antigen would typically be one that is associated with the disease being treated. Thus, in the case of diabetes, the antigen may be, for example, GAD, IA2, or insulin (or a fragment thereof).

Other therapies that are useful according to the subject invention include, but are not limited to:

Anti-T cell (Anti-CD3 [Nuvion, N1-0401, hOKT3 (Ala-Ala)])

Anti-B cell (Rituximab/anti-CD20)

Cell therapies (Treg, personalized DC, autologus BM)

Cytokine modulation (TNF-a blockers, Enbrel, Humira, Remicade)

Costimulatory modulation (anti-CD40; CTLA-41g [Abatacept, Belatacept]

Additional Applications

The combination therapies of the subject invention may also be administered in conjunction with islet transplantation, as well as stem cell treatments and/or treatments that promote conversion of cells into insulin-secreting cells.

Other autoimmune conditions to which the treatments of the subject invention may be applied include, but are not limited to, rheumatoid arthritis, multiple sclerosis, thyroiditis, inflammatory bowel disease, Addison's disease, pancreas transplantation, kidney transplantation, islet transplantation, heart transplantation, lung transplantation, and liver transplantation. In these instances, the cells that are being regenerated and protected are those which are the target of the autoimmune patent. Of particular interest according to the subject invention is the use of the combination therapies of the subject invention to treat autoimmune diseases that can be improved through enhanced functionality of CD4+CD25+T cells.

Timing of Treatment

The combination therapies of the subject invention can be used to reverse type 1 diabetes in, for example, new-onset patients.

In another embodiment, treatment is administered prior to the onset of clinical manifestation of overt type 1 diabetes. The time of administration is preferably before extensive irreversible beta cell destruction as evidenced by for example, the clinical onset of type 1 diabetes.

As set forth in more detail below with respect to type 1 diabetes, those skilled in the art, having the benefit of the instant disclosure can utilize diagnostic assays to assess the stage of disease progression in a patient and then administer treatment at the appropriate time as set forth herein.

With regard to the early detection of type 1 diabetes, numerous autoantibodies have been detected that are present at the onset of type 1 diabetes. Also, new serologic markers associated with type 1 diabetes continue to be described. Four islet autoantibodies appear to be the most useful markers of type 1 diabetes: islet cell antibodies (ICA), insulin autoantibodies (IAA), glutamic acid decarboxylase autoantibodies (GADA), and insulinoma-associated-2 autoantibodies (IA-2A). These are discussed in more detail below; however, the use of these markers to identify those at risk for developing type 1 diabetes is well known to those skilled in the art. In a specific embodiment of the subject invention, treatment is administered when a patient has at least one antibody marker or, preferably, at least two of the antibody markers.

ICA serve an important role as serologic markers of beta-cell autoimmunity. Seventy percent or more of Caucasians are ICA-positive at onset of type 1 diabetes. Following diagnosis, ICA frequency decreases, and fewer than 10% of patients still express ICA after 10 years. The general population frequency of ICA is between 0.1% and 0.3%. In a preferred embodiment of the subject invention, ATG is administered prior to a decrease in ICA.

To date, insulin is the only beta-cell-specific autoantigen. IAA occur in 35-60% of children at onset of type 1 diabetes but are less common in adults. For example, in Australians with new-onset type 1 diabetes, IAA were present in 90% of children less than 5 years old, in 71% of 5-10-year-olds, and in 50% of 10-15-year-olds. In Britons with type 1 diabetes, IAA were identified in 83% of children less than 10 years old and in 56% of children 10 years old and greater.

IAA have been detected in several other autoimmune diseases. IAA were identified in 15.9% of patients with Hashimoto's thyroiditis and 13.5% of Graves' disease subjects. In another study, IAA frequencies in various thyroid autoimmune diseases were 44% in Graves' disease, 21% in primary hypothyroidism, and 23% in chronic autoimmune thyroiditis, compared with 40% in primary adrenal failure, 36% in chronic hepatitis, 40% in pernicious anemia, 25% in rheumatoid arthritis, and 29% in systemic lupus erythematosus.

Approximately 2-3% of the general population express GAD autoantibodies. These antibodies are detected in 60% or more of new-onset cases of type 1 diabetes. The IA-2A and IA-2βA general population frequencies are similar to GADA at 2-3%. IA-2A and IA-2BA are observed in 60% or more of new-onset type 1 diabetes cases.

Early biochemical evidence of beta cell injury is a decreased first-phase insulin response to the administration of intravenous glucose (IVGTT). First-phase response is defined as the insulin concentrations at +1 and +3 min following completion of an intravenous bolus injection of glucose (e.g., 0.5 g/kg). There is also a dissociation in beta cell response to secretagogues: Initially the insulin response to intravenous amino acid administration (e.g., arginine) is preserved even while first-phase responses are deficient (Ganda, O. P. et al., 1984. "Differential sensitivity to beta-cell secretagogues in early, type 1 diabetes mellitus," *Diabetes* 33: 516-521). In ICA-positive individuals eventually developing insulin-dependent diabetes, first-phase insulin release diminishes at a rate of about 20-40 µU/mL/year (Srikanta, S. 1984. "Pre-type 1 diabetes, linear loss of beta cell response to intravenous glucose," *Diabetes* 33: 717-720).

When beta cell mass has substantially declined to less than 50% but more than 10% of normal, the OGTT may display abnormalities such as impaired fasting glucose (110-125 mg/dL) or impaired glucose tolerance (2-h glucose post-75-g challenge: 140-199 mg/dL). An abnormal OGTT prior to the clinical onset of type 1 diabetes is more likely observed in younger children. Frank clinical diabetes usually follows within 1-2 years of the onset of oral glucose intolerance. By the time acute symptoms of type 1 diabetes develop, beta cell mass is believed to have declined by approximately 90% or more from baseline. In one embodiment of the subject invention, treatment is administered once oral glucose intolerance is observed.

Most current procedures for the prediction of type 1 diabetes involve analyses of multiple islet autoantibodies. In every such study reported, nondiabetic individuals who express combinations of islet autoantibodies are found to be at greater risk for type 1 diabetes than individuals who express fewer varieties of islet autoantibodies. In addition, the total number of types of islet autoantibodies is usually more important than the specific combination of islet autoantibodies. In type 1 diabetes subjects, islet autoantibodies can also reappear after pancreas or islet transplantation, predicting failure to become insulin-independent (Bosi, E. et al. 2001.*Diabetes* 50:2464-2471).

Thus, in genetically predisposed individuals, an environmental trigger or triggers are believed to initiate beta cell autoimmunity, which can be identified by the presence of islet autoantibodies. With progressive beta cell damage, there is loss of first-phase insulin response to intravenous glucose administration. Subsequently the OGTT becomes abnormal, followed by symptoms of diabetes and the diagnosis of type 1 diabetes. Clearly the detection of islet autoimmunity can therefore be used as a predictive marker for the subsequent development of type 1 diabetes.

Both in nondiabetic relatives of type 1 diabetes subjects and in the general population, the detection of islet autoantibodies identifies individuals who are at high risk to develop subsequent type 1 diabetes (LaGasse, J. M. et al. 2002. *Diabetes Care* 25:505-511). Higher titers of ICA are more predictive than lower titers, and multiple islet autoantibodies are more powerful predictors than the presence of single autoantibodies. The combination of ICA plus low first-phase insulin secretion is possibly the strongest confirmed predictor of subsequent type 1 diabetes as demonstrated in the DPT-1. When using single autoantibodies, comparative sensitivities for the prediction of type 1 diabetes are as follows: ICA>GADA>IA-2A>>IAA. Combination islet autoantibody assays (e.g., the simultaneous detection of GADA and IA-2A (Sacks, D. B. et al. 2001. *J. Clin. Chem.* 47:803-804; Kawasaki, E. et al. 2000. *Front Biosci.* 5:E181-E190) will likely supersede ICA testing in future testing programs.

The majority of individuals with type 1 diabetes have islet autoantibodies at the time of onset of the disease. In cases where it is difficult to differentiate type1 from type 2 diabetes, the presence of one or more islet autoantibodies (e.g., ICA, IAA, GADA, or IA-2A) is diagnostic of type 1a, immune-mediated diabetes (Rubinstein, P. et al. 1981. *Hum. Immunol.* 3:271-275). When individuals clinically present with a subtle, non-gketotic form of diabetes that may not be insulin-requiring yet are islet autoantibody-positive, LADA is diagnosed.

Formulations and Methods of Administration

Administration of the compositions can be systemic or local. Any route known to those of skill in the art for the administration of a therapeutic composition of the invention is contemplated including, for example, intravenous, intramuscular, subcutaneous or a catheter for long-term administration. Alternatively, it is contemplated that the therapeutic composition may be delivered to the patient at multiple sites. The multiple administrations may be rendered simultaneously or may be administered over a period of several hours. In certain cases, it may be beneficial to provide a continuous flow of the therapeutic composition. Additional therapy may be administered on a period basis, for example, daily, weekly, or monthly.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of oral and parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of the present invention present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the compound of the present invention or its pharmaceutical salt from about 0.1 to about 10% w/v (weight per unit volume).

One of the therapeutic embodiments of the present invention is the provision, to a subject in need thereof, compositions comprising G-CSF. G-CSF may have been generated through recombinant means or by automated peptide synthesis. The G-CSF formulations for such a therapy may be selected based on the route of administration and may include liposome and micelle formulations as well as classic pharmaceutical preparations.

The G-CSF proteins are formulated into appropriate preparation and administered to one or more sites within the subject in a therapeutically effective amount. In particularly preferred embodiments, the human G-CSF protein-based therapy is effected via continuous or intermittent intravenous administration.

Those of skill in the art will understand that the amounts of human G-CSF polypeptides administered for therapeutic use may vary. It is contemplated that the specific activity of the human G-CSF protein preparation may be in the range of about 100 units/mg of protein to about 500 units/mg protein. Preferably, the protein composition is substantially free of contaminating factors, contamination level of less than 0.02% (w/w). Human G-CSF compositions, suitable for injection into a patient, can be prepared, for example, by reconstitution with a pharmacologically acceptable diluent of a lyophilized sample comprising purified human G-CSF and stabilizing salts.

The combination therapy compositions would be provided in a combined amount effective to produce the desired therapeutic outcome. This may be achieved by administering a single composition or pharmacological formulation that includes multiple agents, or by administering two or more distinct compositions or formulations, at the same time. In one embodiment, the various components are separately containerized but provided together as a combination therapy kit.

Alternatively, one treatment may precede or follow another agent treatment by intervals ranging from minutes to weeks. In embodiments where the therapeutic agents are administered separately, one would generally ensure that a significant period of time did not expire between the times of each delivery, such that the agents would still be able to exert an advantageously combined effect. In such instances, it is contemplated that one would administer the multiple modalities within about 12-24 hours of each other and, more preferably, within about 6 12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

As used herein, the term "effective amount" of a compound of the present invention refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of the present invention, a number of factors are considered by the attending diagnostician, including, but not limited to: the compound of the present invention to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of the present invention is expected to vary from about 0.01 milligram per kilogram of body weight per day (mg/kg/day) to about 50 mg/kg/day, and preferable from 0.1 milligram per kilogram of body weight per day (mg/kg/day) to about 20 mg/kg/day. More preferred amounts can be determined by one skilled in the art.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for treating type 1 diabetes wherein said method comprises administering, to a patient in need of such treatment, a combination therapy, wherein the combination therapy consists of administering anti-thymocyte globulin (ATG) and granulocyte colony-stimulating factor (G-CSF); and optionally,
one or more additional agents selected from stem cells, agents that reduce a pathological autoimmune response, exenatide, DPPIV inhibitors, EGF, INGAP, a local cytokine, alpha-1 antitrypsin (AAT), vitamin D, anti-oxidants, anti-inflammatory agents, glulisine, glucagons, modulators of cytokines, anti-apoptotic molecules, exendin-4, carriers, adjuvants, binders, diluents, excipients, lubricants, glidants, flavoring agents, preservatives, coloring agents, chelating agents, buffers, and agents for the adjustment of tonicity.

2. The method, according to claim 1, wherein the combination therapy consists of administering anti-thymocyte globulin (ATG), granulocyte colony-stimulating factor (G-CSF), and rapamycin; and optionally,
one or more additional agents selected from stem cells, agents that reduce a pathological autoimmune response, exenatide, DPPIV inhibitors, EGF, INGAP, a local cytokine, alpha-1 antitrypsin (AAT), vitamin D, anti-oxidants, anti-inflammatory agents, glulisine, glucagons, modulators of cytokines, anti-apoptotic molecules, exendin-4, carriers, adjuvants, binders, diluents, excipients, lubricants, glidants, flavoring agents, preservatives, coloring agents, chelating agents, buffers, and agents for the adjustment of tonicity.

3. The method, according to claim 1, wherein the combination therapy consists of administering anti-thymocyte globulin (ATG), granulocyte colony-stimulating factor (G-CSF), and stem cells, and optionally,
one or more additional agents selected from agents that reduce a pathological autoimmune response, exenatide, DPPIV inhibitors, EGF, INGAP, a local cytokine, alpha-1 antitrypsin (AAT), vitamin D, anti-oxidants, anti-inflammatory agents, glulisine, glucagons, modulators of cytokines, anti-apoptotic molecules, exendin-4, carriers, adjuvants, binders, diluents, excipients, lubricants, glidants, flavoring agents, preservatives, coloring agents, chelating agents, buffers, and agents for the adjustment of tonicity.

4. The method, according to claim 3, wherein the stem cells are mescenchymal stem cells (MSC).

5. The method, according to claim 1, wherein the combination therapy consists of administering anti-thymocyte globulin (ATG), granulocyte colony-stimulating factor (G-CSF), and one or more agents selected from exenatide, DPPIV inhibitors, EGF, INGAP and a local cytokine; and optionally
one or more additional agents selected from stem cells, agents that reduce a pathological autoimmune response, alpha-1 antitrypsin (AAT), vitamin D, anti-oxidants, anti-inflammatory agents, glulisine, glucagons, modulators of cytokines, anti-apoptotic molecules, exendin-4 carriers, adjuvants, binders, diluents, excipients, lubricants, glidants, flavoring agents, preservatives, coloring agents, chelating agents, buffers, and agents for the adjustment of tonicity.

6. The method, according to claim 1, wherein the combination therapy consists of administering anti-thymocyte globulin (ATG), granulocyte colony-stimulating factor (G-CSF), and one or more agents selected from alpha-1 antitrypsin (AAT), vitamin D, anti-oxidants, anti-inflammatory agents and modulators of cytokines; and optionally,
one or more additional agents selected from stem cells, agents that reduce a pathological autoimmune response, exenatide, DPPIV inhibitors, EGF, INGAP, a local cytokine, glulisine, glucagons, anti-apoptotic molecules, exendin-4, carriers, adjuvants, binders, diluents, excipients, lubricants, glidants, flavoring agents, preservatives, coloring agents, chelating agents, buffers, and agents for the adjustment of tonicity.

7. The method, according to claim 1, wherein the combination therapy consists of administering anti-thymocyte globulin (ATG), granulocyte colony-stimulating factor (F-CSF), and one or more agents selected from glulisine, glucagons, DPP4 inhibitors, anti-apoptotic molecules and exendin-4; and optionally,
one or more additional agents selected from stem cells, agents that reduce a pathological autoimmune response, exenatide, DPPIV inhibitors, EGF, INGAP, a local cytokine, alpha-1 antitrypsin AAT), vitamin D, anti-oxidants, anti-inflammatory agents, modulators of cytokines, carriers, adjuvants, binders, diluents, excipients, lubricant, glidants, flavoring agents, preservatives, coloring agents, chelating agents, buffers, and agents for the adjustment of tonicity.

8. The method, according to claim 7, wherein the glucagon is glucagon-like peptide-1 (GLP-1).

9. The method according to claim 1, wherein the therapy is administered prior to a clinical manifestation of type 1 diabetes.

10. The method, according to claim 1, wherein the combination therapy is administered to a patient who has been determined to have at least one of the following: islet cell antibodies (ICA), insulin autoantibodies (IAA), glutamic acid decarboxylase antibodies (GADA), and insulinoma-associated-2-autoantibodies (IA-2A).

11. The method, according to claim 10, wherein the patient has at least two of the listed antibodies.

12. The method, according to claim 1, wherein the patient has been determined to have a decreased first-phase insulin response to the administration of intravenous glucose.

13. The method, according to claim 1, wherein beta cell mass of the patient has declined to less than 50% but more than 10% of normal.

14. The method, according to claim 1, wherein the patient has been determined to be genetically pre-disposed to type 1 diabetes.

15. The method, according to claim 1, wherein the therapy is done in conjunction with islet transplantation.

16. The method, according to claim 1, wherein the administration of the therapeutic agents is oral and/or parenteral.

\* \* \* \* \*

UNITED STATES PATENT AND TRADEMARK OFFICE
CERTIFICATE OF CORRECTION

PATENT NO. : 8,758,761 B2  
APPLICATION NO. : 12/680614  
DATED : June 24, 2014  
INVENTOR(S) : Mark Atkinson et al.

Page 1 of 1

It is certified that error appears in the above-identified patent and that said Letters Patent is hereby corrected as shown below:

In the Specification

Column 6,  
Line 7, "hoiiiione is" should read --hormone is--.

Column 6,  
Line 17, "epideiinal" should read --epidermal--.

Column 6,  
Line 37, "Other (no new paragraph)" should read --Other (new paragraph)--.

Column 8,  
Line 2, "and IA-2BA" should read --and IA-2ßA--.

In the Claims

Column 12, Claim 7,  
Line 50-51, "factor (F-CSF)," should read --factor (G-CSF),--.

Signed and Sealed this  
Twenty-eighth Day of October, 2014

Michelle K. Lee  
*Deputy Director of the United States Patent and Trademark Office*